(12) United States Patent
Yamago et al.

(10) Patent No.: US 11,427,538 B2
(45) Date of Patent: Aug. 30, 2022

(54) ORGANIC TELLURIUM COMPOUND, METHOD FOR PRODUCING SAME, LIVING RADICAL POLYMERIZATION INITIATOR, METHOD FOR PRODUCING VINYL POLYMER, AND VINYL POLYMER

(71) Applicants: Kyoto University, Kyoto (JP); OTSUKA CHEMICAL CO., LTD., Osaka (JP)

(72) Inventors: Shigeru Yamago, Kyoto (JP); Osamu Ito, Tokushima (JP)

(73) Assignees: KYOTO UNIVERSITY, Kyoto (JP); OTSUKA CHEMICAL CO., LTD., Osaka (JP)

( * ) Notice: Subject to any disclaimer, the term of this patent is extended or adjusted under 35 U.S.C. 154(b) by 502 days.

(21) Appl. No.: 16/608,221

(22) PCT Filed: Apr. 23, 2018

(86) PCT No.: PCT/JP2018/016404
§ 371 (c)(1),
(2) Date: Oct. 25, 2019

(87) PCT Pub. No.: WO2018/199000
PCT Pub. Date: Nov. 1, 2018

(65) Prior Publication Data
US 2020/0048192 A1 Feb. 13, 2020

(30) Foreign Application Priority Data
Apr. 28, 2017 (JP) .............. JP2017-089092

(51) Int. Cl.
*C07C 395/00* (2006.01)
*C08F 4/06* (2006.01)

(52) U.S. Cl.
CPC .............. *C07C 395/00* (2013.01); *C08F 4/06* (2013.01)

(58) Field of Classification Search
CPC ................................... C07C 395/00
See application file for complete search history.

(56) References Cited

U.S. PATENT DOCUMENTS

| | | | | |
|---|---|---|---|---|
| 2005/0245714 A1* | 11/2005 | Yamago | ............... | C08F 257/00 562/899 |
| 2006/0135711 A1* | 6/2006 | Yamago | ................ | C08F 4/04 526/89 |
| 2006/0167199 A1 | 7/2006 | Yamago et al. | | |
| 2006/0199927 A1 | 9/2006 | Yamago et al. | | |
| 2007/0298124 A1* | 12/2007 | Albeck | ................ | A61P 17/18 424/650 |
| 2008/0004366 A1 | 1/2008 | Yamago et al. | | |
| 2008/0009597 A1 | 1/2008 | Yamago et al. | | |
| 2010/0267998 A1* | 10/2010 | Uhlenbrock | ........ | C07C 395/00 568/840 |

FOREIGN PATENT DOCUMENTS

| | | | |
|---|---|---|---|
| JP | 59176294 A | * | 10/1984 |
| JP | 04360829 A | * | 12/1992 |
| JP | 2006-225524 A | | 8/2006 |
| JP | 2008-247919 A | | 10/2008 |
| JP | 2016-204529 A | | 12/2016 |
| WO | 2004/014848 A1 | | 2/2004 |
| WO | 2004/014962 A1 | | 2/2004 |
| WO | 2004/072126 A1 | | 8/2004 |
| WO | 2004/096870 A1 | | 11/2004 |

OTHER PUBLICATIONS

Yamago, Shigeru et al.; "Organotellurium Compounds as Novel Initiators for Controlled/Living Radical Polymerizations. Synthesis of Functionalized Polystyrenes and End-Group Modifications", J.AM.CHEM.SOC. vol. 124, No. 12, 2002, pp. 2874-2875. cited in CN Office Action dated Oct. 22, 2020.
Office Action dated Oct. 22, 2020 issued in counterpart CN application No. 201880024244 with English translation. (16 pages).
Extended (Supplementary) European Search Report dated Dec. 10, 2020, issued in counterpart application No. 18792072.3. (5 pages).
Fan, Weijia et al.; "Synthesis of Multivalent Organotellurium Chain-Tranfer Agents by Post-modification and Their Applications in Living Radical Polymerization", HHS Public Access. Chemistry, vol. 22, No. 47, Nov. 14, 2016, pp. 17006-17010. Cited in Extended (Supplementary) European Search Report dated Dec. 10, 2020.
Written Opinion (Form PCT/ISA/237) of the International Searching Authority dated Jul. 17, 2018, issued in counterpart International Application No. PCT/JP2018/016404, with English translation (8 pages).

(Continued)

*Primary Examiner* — Amanda C. Walke
(74) *Attorney, Agent, or Firm* — WHDA, LLP

(57) ABSTRACT

An organic tellurium compound is disclosed having a versatility that, when used as a living radical polymerization initiator, it is applicable to polymerization of a vinyl monomer in an aqueous vehicle without using any surfactant or dispersant. The organic tellurium compound is represented by a general formula (1),

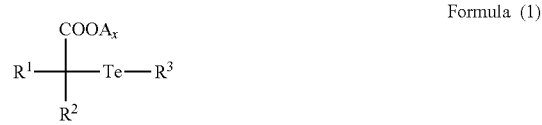

Formula (1)

where $R^1$ and $R^2$ each independently represent a hydrogen atom or an alkyl group having 1 to 8 carbon atoms, A represents an alkali metal atom or an alkaline earth metal atom, x=1 when A is monovalent, x=½ when A is divalent, and $R^3$ is represented by a general formula (2),

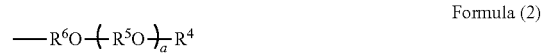

Formula (2)

where in the general formula (2) $R^4$ represents a hydrogen atom or an alkyl group having 1 to 8 carbon atoms, $R^5$ and $R^6$ each independently represent an alkylene group having 2 to 8 carbon atoms, and a represents an integer from 0 to 10.

7 Claims, No Drawings

(56) References Cited

OTHER PUBLICATIONS

Kayahara, et al.; "Optimization of Organotellurium Transfer Agents for Highly Controlled Living Radical Polymerization", Macromolecules, 2008, 41 (3), pp. 527-529 (3 pages), cited in ISR.
International Search Report dated Jul. 17, 2018, issued in counterpart International Application No. PCT/JP2018/016404 (2 page).
Written Opinion (Form PCT/ISA/237) of the International Searching Authority dated Jul. 17, 2018, issued in counterpart International Application No. PCT/JP2018/016404 (7 pages).

\* cited by examiner

ORGANIC TELLURIUM COMPOUND, METHOD FOR PRODUCING SAME, LIVING RADICAL POLYMERIZATION INITIATOR, METHOD FOR PRODUCING VINYL POLYMER, AND VINYL POLYMER

TECHNICAL FIELD

The present invention relates to organic tellurium compounds and methods for producing the same, living radical polymerization initiators using the organic tellurium compounds and methods for producing vinyl polymers, and vinyl polymers obtained by the methods for producing vinyl polymers.

BACKGROUND ART

Living radical polymerization processes are polymerization processes that enable precise control of molecular structures and production of polymers having a homogeneous composition while keeping the convenience and versatility of conventional radical polymerization processes, and demonstrate superior performance on production of novel polymeric materials. Therefore, living radical polymerization techniques have recently progressed greatly and living radical polymerization processes using various approaches have been reported. Among them, the TERP (organotellurium-mediated living radical polymerization) process is a polymerization process to which particular attention has been paid in its versatility that it is applicable to polymerization of various types of vinyl monomers and in that it can highly control the molecular weights and molecular weight distributions of polymers under practical reaction conditions no different from normal radical polymerization (see Patent Literatures 1 to 4).

The TERP processes disclosed in Patent Literatures 1 to 4 are performed in a system in which a bulk material or an organic solvent is used. From the environmental and industrial viewpoints, there is demand for applicability of a TERP process to aqueous vehicles. To this end, Patent Literature 5 proposes that a surfactant and/or a dispersant is used in an aqueous vehicle.

CITATION LIST

Patent Literature

Patent Literature 1: WO 2004/014848
Patent Literature 2: WO 2004/014962
Patent Literature 3: WO 2004/072126
Patent Literature 4: WO 2004/096870
Patent Literature 5: JP-A-2006-225524

SUMMARY OF INVENTION

Technical Problem

The organic tellurium compounds disclosed in Patent Literatures 1 to 5 dissolve sparingly in water and therefore have a problem of unsuitableness for polymerization of water-soluble vinyl monomers in aqueous vehicles. Furthermore, in the method disclosed in Patent Literature 5, the surfactant or the dispersant may remain in the resultant polymer.

An object of the present invention is to provide an organic tellurium compound having a versatility that, when used as a living radical polymerization initiator, it is applicable to polymerization of a vinyl monomer in an aqueous vehicle without using any surfactant or dispersant, a method for producing the organic tellurium compound, a living radical polymerization initiator using the organic tellurium compound, a method for producing a vinyl polymer using the organic tellurium compound, and a vinyl polymer obtained by the method for producing a vinyl polymer.

Solution to Problem

The present invention provides an organic tellurium compound and a method for producing the same, a living radical polymerization initiator, a method for producing a vinyl polymer, and a vinyl polymer, as given below.

Aspect 1: An organic tellurium compound represented by the following general formula (1):

[Chem. 1]

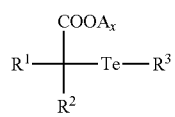

Formula (1)

where in the general formula (1) $R^1$ and $R^2$ each independently represent a hydrogen atom or an alkyl group having 1 to 8 carbon atoms, A represents an alkali metal atom or an alkaline earth metal atom, x=1 when A is monovalent, x=½ when A is divalent, and $R^3$ is represented by the following general formula (2), general formula (3) or general formula (4):

[Chem. 2]

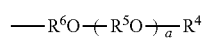

Formula (2)

where in the general formula (2) $R^4$ represents a hydrogen atom or an alkyl group having 1 to 8 carbon atoms, $R^5$ and $R^6$ each independently represent an alkylene group having 2 to 8 carbon atoms, and a represents an integer from 0 to 10,

[Chem. 3]

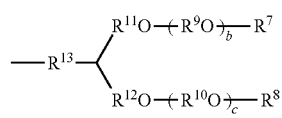

Formula (3)

where in the general formula (3) $R^7$ and $R^8$ each independently represent a hydrogen atom or an alkyl group having 1 to 8 carbon atoms, $R^9$, $R^{10}$, $R^{11}$, and $R^{12}$ each independently represent an alkylene group having 2 to 8 carbon atoms, $R^{13}$ represents an alkylene group having 1 to 8 carbon atoms, and b and c each independently represent an integer from 0 to 10,

[Chem. 4]

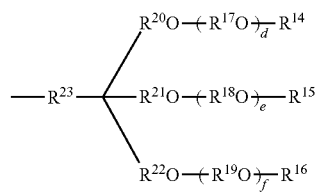

Formula (4)

where in the general formula (4) $R^{14}$, $R^{15}$, and $R^{16}$ each independently represent a hydrogen atom or an alkyl group having 1 to 8 carbon atoms, $R^{17}$, $R^{18}$, $R^{19}$, $R^{20}$, $R^{21}$, and $R^{22}$ each independently represent an alkylene group having 2 to 8 carbon atoms, $R^{23}$ represents an alkylene group having 1 to 8 carbon atoms, and d, e, and f each independently represent an integer from 0 to 10.

Aspect 2: A method for producing the organic tellurium compound according to aspect 1, the method including the steps of: (A) reacting a compound represented by a general formula (5) below with a base; (B) reacting a compound obtained by the step (A) with a compound represented by a general formula (6) below; (C) removing a protective group on a carboxyl group in a compound obtained by the step (B), thus deprotecting the carboxyl group; and (D) neutralizing a carboxylic acid obtained by the step (C):

[Chem. 5]

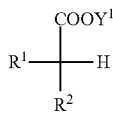

Formula (5)

where in the general formula (5) $R^1$ is the same as $R^1$ in the general formula (1), $R^2$ is the same as $R^2$ in the general formula (1), and $Y^1$ represents a protecting group,

[Chem. 6]

Formula (6)

where in the general formula (6) $R^3$ is the same as $R^3$ in the general formula (1), and X represents a halogen atom.

Aspect 3: A living radical polymerization initiator made of the organic tellurium compound according to aspect 1.

Aspect 4: A method for producing a vinyl polymer, the method including the step of polymerizing a vinyl monomer by a living radical polymerization using the organic tellurium compound according to aspect 1 to synthesize a vinyl polymer.

Aspect 5: The method for producing a vinyl polymer according to aspect 4, wherein the vinyl monomer is a water-soluble vinyl monomer.

Aspect 6: The method for producing a vinyl polymer according to aspect 4 or 5, wherein the living radical polymerization is performed in an aqueous vehicle.

Aspect 7: A vinyl polymer obtained by the method for producing a vinyl polymer according to any one of aspects 4 to 6.

Advantageous Effects of Invention

The present invention enables provision of an organic tellurium compound having a versatility that, when used as a living radical polymerization initiator, it is applicable to polymerization of a vinyl monomer in an aqueous vehicle without using any surfactant or dispersant.

DESCRIPTION OF EMBODIMENTS

Hereinafter, a description will be given of an example of a preferred embodiment for working of the present invention. However, the following embodiment is simply illustrative. The present invention is not at all limited by the following embodiment.

<Organic Tellurium Compound>

An organic tellurium compound according to the present invention is represented by the following general formula (1).

[Chem. 7]

Formula (1)

In the above general formula (1), the groups represented by $R^1$ and $R^2$ are each independently a hydrogen atom or an alkyl group having 1 to 8 carbon atoms and are specifically as follows.

Examples of the alkyl group represented by $R^1$ and $R^2$ and having 1 to 8 carbon atoms include: a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, and other linear or branched alkyl groups; and a cyclohexyl group and other cyclic alkyl groups. Preferred are linear or branched alkyl groups having 1 to 4 carbon atoms and more preferred are a methyl group and an ethyl group.

In the above general formula (1), A represents an alkali metal atom or an alkaline earth metal atom. Examples of the alkali metal atom include lithium, sodium, potassium, rubidium, cesium, and francium and preferred alkali metal atoms are sodium and potassium. Examples of the alkaline earth metal atom include beryllium, magnesium, calcium, strontium, barium, and radium and preferred alkaline earth metal atoms are magnesium and calcium.

In the above general formula (1), x=1 when A is monovalent, and x=½ when A is divalent.

In the above general formula (1), $R^3$ is a group represented by the following general formula (2), general formula (3) or general formula (4) and preferably a group represented by the general formula (2).

[Chem. 8]

Formula (2)

In the above general formula (2), the group represented by $R^4$ is a hydrogen atom or an alkyl group having 1 to 8 carbon atoms, preferably an alkyl group having 1 to 8 carbon atoms, and specifically as follows.

Examples of the alkyl group represented by $R^4$ and having 1 to 8 carbon atoms include a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, and other linear or branched alkyl groups. Preferred are linear or branched alkyl groups having 1 to 4 carbon atoms and more preferred are a methyl group and an ethyl group.

In the above general formula (2), the groups represented by $R^5$ and $R^6$ are each independently an alkylene group having 2 to 8 carbon atoms and are specifically as follows.

Examples of the alkylene group represented by $R^5$ and $R^6$ and having 2 to 8 carbon atoms include an ethylene group, an n-propylene group, an isopropylene group, an n-butylene group, an isobutylene group, a sec-butylene group, a tert-butylene group, a pentylene group, a hexylene group, a heptylene group, an octylene group, and other linear or branched alkylene groups. Preferred are linear alkylene groups having 2 to 5 carbon atoms and more preferred are an ethylene group and an n-propylene group.

In the above general formula (2), a is an integer from 0 to 10, preferably an integer from 1 to 5, and more preferably an integer from 1 to 3.

[Chem. 9]

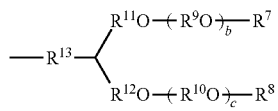

Formula (3)

In the above general formula (3), the groups represented by $R^7$ and $R^8$ are each independently a hydrogen atom or an alkyl group having 1 to 8 carbon atoms, preferably an alkyl group having 1 to 8 carbon atoms, and specifically as follows.

Examples of the alkyl group represented by $R^7$ and $R^8$ and having 1 to 8 carbon atoms include a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, and other linear or branched alkyl groups. Preferred are linear or branched alkyl groups having 1 to 4 carbon atoms and more preferred are a methyl group and an ethyl group.

In the above general formula (3), the groups represented by $R^9$ to $R^{12}$ are each independently an alkylene group having 2 to 8 carbon atoms and are specifically as follows.

Examples of the alkylene group represented by $R^9$ to $R^{12}$ and having 2 to 8 carbon atoms include an ethylene group, an n-propylene group, an isopropylene group, an n-butylene group, an isobutylene group, a sec-butylene group, a tert-butylene group, a pentylene group, a hexylene group, a heptylene group, an octylene group, and other linear or branched alkylene groups. Preferred are linear alkylene groups having 2 to 5 carbon atoms and more preferred are an ethylene group and an n-propylene group.

In the above general formula (3), the group represented by $R^{13}$ is an alkylene group having 1 to 8 carbon atoms and is specifically as follows.

Examples of the alkylene group represented by $R^{13}$ and having 1 to 8 carbon atoms include a methylene group, an ethylene group, an n-propylene group, an isopropylene group, an n-butylene group, an isobutylene group, a sec-butylene group, a tert-butylene group, a pentylene group, a hexylene group, a heptylene group, an octylene group, and other linear or branched alkylene groups. Preferred are linear alkylene groups having 1 to 5 carbon atoms and more preferred are a methylene group, an ethylene group, and an n-propylene group.

In the above general formula (3), b and c are each independently an integer from 0 to 10, preferably an integer from 1 to 5, and more preferably an integer from 1 to 3.

[Chem. 10]

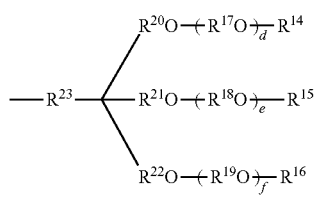

Formula (4)

In the above general formula (4), the groups represented by $R^{14}$ to $R^{16}$ are each independently a hydrogen atom or an alkyl group having 1 to 8 carbon atoms, preferably an alkyl group having 1 to 8 carbon atoms, and specifically as follows.

Examples of the alkyl group represented by $R^{14}$ to $R^{16}$ and having 1 to 8 carbon atoms include a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, and other linear or branched alkyl groups. Preferred are linear or branched alkyl groups having 1 to 4 carbon atoms and more preferred are a methyl group and an ethyl group.

In the above general formula (4), the groups represented by $R^{17}$ to $R^{22}$ are each independently an alkylene group having 2 to 8 carbon atoms and are specifically as follows.

Examples of the alkylene group represented by $R^{17}$ to $R^{22}$ and having 2 to 8 carbon atoms include an ethylene group, an n-propylene group, an isopropylene group, an n-butylene group, an isobutylene group, a sec-butylene group, a tert-butylene group, a pentylene group, a hexylene group, a heptylene group, an octylene group, and other linear or branched alkylene groups. Preferred are linear alkylene groups having 2 to 5 carbon atoms and more preferred are an ethylene group and an n-propylene group.

In the above general formula (4), the group represented by $R^{23}$ is an alkylene group having 1 to 8 carbon atoms and is specifically as follows.

Examples of the alkylene group represented by $R^{23}$ and having 1 to 8 carbon atoms include a methylene group, an ethylene group, an n-propylene group, an isopropylene group, an n-butylene group, an isobutylene group, a sec-butylene group, a tert-butylene group, a pentylene group, a hexylene group, a heptylene group, an octylene group, and other linear or branched alkylene groups. Preferred are linear alkylene groups having 1 to 5 carbon atoms and more preferred are a methylene group, an ethylene group, and an n-propylene group.

In the above general formula (4), d, e, and f are each independently an integer from 0 to 10, preferably an integer from 1 to 5, and more preferably an integer from 1 to 3.

<Method for Producing Organic Tellurium Compound>

The organic tellurium compound represented by the above general formula (1) can be produced, for example, by a production method including the steps of: (A) reacting a compound represented by a general formula (5) below with a base; (B) reacting a compound obtained by the step (A) with a compound represented by a general formula (6) below; (C) removing a protecting group on a carboxyl group in a compound obtained by the step (B), thus deprotecting the carboxyl group; and (D) neutralizing a carboxylic acid obtained by the step (C).

[Chem. 11]

Formula (5)

In the above general formula (5), the group represented by $R^1$ is the same group as $R^1$ in the above general formula (1). In the above general formula (5), the group represented by $R^2$ is the same group as $R^2$ in the above general formula (1).

In the above general formula (5), $Y^1$ represents a protecting group. No particular limitation is placed on the type of the protecting group so long as it is a known group that can be used as a protecting group for a carboxyl group. Examples of the protecting group include: trialkylsilyl groups, such as a trimethylsilyl group, a dimethylbutylsilyl group, and a triethylsilyl group; 1-alkoxyalkyl groups, such as a 1-ethoxyethyl group and a 1-propoxyethyl group; and cyclic 1-alkoxyalkyl groups, such as a tetrahydrofuranyl group, a tetrahydropyranyl group, and a triphenylmethyl group.

[Chem. 12]

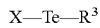

Formula (6)

In the above general formula (6), the group represented by $R^3$ is the same group as $R^3$ in the above general formula (1).

In the above general formula (6), the group represented by X is a halogen atom. Examples of the halogen atom include a fluorine atom, a chlorine atom, a bromine atom, and an iodine atom. Preferred are a chlorine atom and a bromine atom.

As described above, the step (A) is the step of reacting a compound represented by the above general formula (5) with a base.

Examples of the base that can be used in the step (A) include lithium diisopropylamide, hexamethyldisilazane lithium, lithium tetramethylpiperidine, lithium amide, potassium diisopropylamide, potassium amide, sodium isopropylamide, and sodium amide. Preferred among them is lithium diisopropylamide.

The base for use in the step (A) is prepared in a solvent. Examples of the solvent that can be used include: polar solvents, such as dimethylformamide (DMF); aromatic solvents, such as toluene and xylene; aliphatic hydrocarbons, such as hexane and dimethoxyethane; and ethereal solvents, such as diethyl ether and tetrahydrofuran (THF). The preferred solvent is THF. The amount of solvent used is appropriately adjusted, but is, generally, preferably 5 ml to 500 ml and more preferably 10 ml to 100 ml relative to 1 g of the base.

The compound represented by the general formula (5) is slowly added dropwise to the base prepared in the above manner and the mixture is stirred. Thus, the compound represented by the general formula (5) and the base are reacted with each other. The reaction time varies according to the reaction temperature, but is, generally, preferably 5 minutes to 24 hours and more preferably 10 minutes to 3 hours. The reaction temperature is preferably −150° C. to 50° C. and more preferably −80° C. to 0° C.

The step (B) is the step of reacting a compound obtained by the step (A) with a compound represented by the above general formula (6).

The compound represented by the above general formula (6) is added to the reaction liquid (compound) obtained by the step (A) and the mixture is stirred. Thus, the compound obtained by the step (A) and the compound represented by the above general formula (6) are reacted with each other. The reaction time varies according to the reaction temperature, but is, generally, preferably 5 minutes to 24 hours and more preferably 10 minutes to 3 hours. The reaction temperature is preferably −150° C. to 50° C. and more preferably −80° C. to 20° C.

After the completion of the reaction, the solvent is concentrated to isolate and purify a desired product. Before the solvent concentration, washing with water, brine or the like may be appropriately performed. The purification method can be appropriately selected depending on the compound, but is generally preferably effected by distillation under reduced pressure, recrystallization or so on.

The step (C) is the step of removing a protecting group on a carboxyl group in the compound obtained by the step (B), thus deprotecting the carboxyl group. The step (C) is preferably performed in the presence of an acidic catalyst.

Examples of the acidic catalyst to be used in the step (C) include: inorganic acids, such as hydrochloric acid, sulfuric acid, nitric acid, and phosphoric acid; and organic acids, such as formic acid, acetic acid, propionic acid, trifluoroacetic acid, methanesulfonic acid, ethanesulfonic acid, propanesulfonic acid, trifluoromethylsulfonic acid, and para-toluenesulfonic acid. Hydrochloric acid and sulfuric acid are preferred because they have a more sufficient pH to make a deprotection reaction and are inexpensively procurable. The above acids may be used singly or in a mixture of two or more of them.

The amount of the acidic catalyst used is preferably 0.01 times to 10 times larger than the amount of substance of carboxyl groups in the compound obtained by the step (B) for use as a source material. Within this range, the deprotection reaction of carboxyl groups can be more sufficiently promoted.

A solvent may be used in the step (C). Examples of the solvent that can be used include water, methanol, ethanol, isopropanol, N,N-dimethylformamide, N,N-dimethylacetamide, acetonitrile, tetrahydrofuran, and acetone. The amount of solvent used is appropriately adjusted, but is, generally, preferably 5 ml to 100 ml relative to 1 g of the compound obtained by the step (B).

In the step (C), an acidic catalyst is added to a solution of the compound obtained by the step (B) and the mixture is stirred. Thus, protecting groups on carboxyl groups in the compound obtained by the step (B) are removed to deprotect the carboxyl groups. The reaction time varies according to the reaction temperature, but is, generally, preferably 5 minutes to 24 hours. The reaction temperature is preferably 0° C. to 50° C.

After the completion of the reaction, the solvent is concentrated to isolate and purify a desired product. Before the solvent concentration, washing with water, brine or the like may be appropriately performed. The purification method can be appropriately selected depending on the compound, but is generally preferably effected by distillation under reduced pressure, recrystallization or so on.

The step (D) is the step of neutralizing a carboxylic acid obtained by the step (C). Example of a base to be used for neutralization of the carboxylic acid include: hydroxides of alkali metals, such as sodium hydroxide and potassium hydroxide; and carbonates of alkali metals, such as sodium carbonate and sodium hydrogen carbonate.

A solvent may be used in the step (D). Examples of the solvent that can be used include water, methyl alcohol, and ethyl alcohol. The amount of solvent used is appropriately adjusted, but is, generally, preferably 5 ml to 100 ml relative to 1 g of the carboxylic acid obtained by the step (C).

In the step (D), a base is added to a solution of the carboxylic acid obtained by the step (C) and the mixture is stirred. Thus, the carboxylic acid obtained by the step (C) is neutralized. The reaction time varies according to the reaction temperature, but is, generally, preferably 5 minutes to 2 hours. The reaction temperature is preferably 0° C. to 50° C.

After the completion of the reaction, the solvent is concentrated to isolate and purify a desired product. Before the solvent concentration, washing with water, brine or the like may be appropriately performed. The purification method can be appropriately selected depending on the compound, but is generally preferably effected by distillation under reduced pressure, recrystallization or so on.

(Method for Producing Compound Represented by General Formula (6))

A compound represented by the above general formula (6) can be produced by reacting an organic ditellurium compound represented by the general formula (7) below with a halogenating agent.

[Chem. 13]

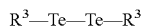

$$R^3\text{—Te—Te—}R^3 \quad \text{Formula (7)}$$

In the general formula (7), the group represented by $R^3$ is the same group as $R^3$ in the above general formula (1).

Examples of the halogenating agent include chlorine, bromine, and iodine. The preferred halogenating agent is bromine.

A specific example of the method for producing a compound represented by the above general formula (6) is the method given as an example below.

First, an organic ditellurium compound represented by the above general formula (7) is dissolved in a solvent. Examples of the solvent that can be used include: polar solvents, such as dimethylformamide (DMF); aromatic solvents, such as toluene and xylene; aliphatic hydrocarbons, such as hexane and dimethoxyethane; and ethereal solvents, such as diethyl ether and tetrahydrofuran (THF).

The amount of solvent used is appropriately adjusted, but is, generally, preferably 5 ml to 500 ml relative to 1 g of the organic ditellurium compound represented by the general formula (7).

Next, a halogenating agent is added to the solvent and the mixture is stirred. Thus, a compound represented by the above general formula (6) can be obtained. The reaction time varies according to the reaction temperature, but is, generally, preferably 5 minutes to 24 hours. The reaction temperature is preferably −50° C. to 50° C.

The solution of the compound represented by the general formula (6), which has been obtained in the above manner, may be used as it is for production of an organic tellurium compound represented by the general formula (1) or the compound isolated and purified from the solution may be used.

(Method for Producing Organic Ditellurium Compound Represented by General Formula (7))

An organic ditellurium compound represented by the above general formula (7) can be produced by reacting ditelluride dianions obtained by reducing metallic tellurium with a compound $R^3$—Z (where the group represented by $R^3$ is the same group as $R^3$ in the general formula (1) and Z represents a halogen atom or a tosylate group).

Examples of a reductant that can be used include metallic sodium, metallic lithium, metallic potassium, and naphthalenides of these metals. The preferred reductant is metallic sodium.

In a method for producing an organic ditellurium compound represented by the above general formula (7), first, metallic tellurium is suspended in a solvent. Examples of the solvent that can be used include ethereal solvents, such as tetrahydrofuran (THF), and ethylenediamine. The preferred solvent is ethylenediamine. The amount of solvent used is appropriately adjusted, but is, generally, preferably 5 ml to 500 ml relative to 1 g of metallic tellurium.

Next, a reductant is added to the suspension and the mixture is stirred. The reaction time varies according to the reaction temperature, but is, generally, preferably 5 minutes to 24 hours. The reaction temperature is preferably 0° C. to 150° C.

Next, the above-mentioned compound $R^3$—Z is slowly added dropwise to the obtained solution of ditelluride dianions and the mixture is stirred. Thus, an organic ditellurium compound represented by the above general formula (7) is obtained. The reaction time varies according to the reaction temperature, but is, generally, preferably 5 minutes to 24 hours. The reaction temperature is preferably −50° C. to 50° C.

After the completion of the reaction, the solvent is concentrated to isolate and purify a desired product. Before the solvent concentration, washing with water, brine or the like may be appropriately performed. The purification method can be appropriately selected depending on the compound, but is generally preferably effected by distillation under reduced pressure, recrystallization or so on.

<Method for Producing Vinyl Polymer and Vinyl Polymer>

A method for producing a vinyl polymer according to the present invention is a production method including the step (I) of polymerizing a vinyl monomer by a living radical polymerization using an organic tellurium compound represented by the above general formula (1) to synthesize a vinyl polymer.

The above living radical polymerization is a living radical polymerization using as a living radical polymerization initiator an organic tellurium compound represented by the general formula (1), in which case, depending on the type of the vinyl monomer and for the purpose of promoting the reaction, controlling the molecular weight or other purposes, polymerization may be performed by further adding an azo polymerization initiator and/or an organic ditellurium compound represented by above general formula (7).

Specifically, examples are methods for polymerizing the vinyl monomer using one of the following compounds (a) to (d) to produce a vinyl polymer.

(a) an organic tellurium compound represented by the general formula (1), (b) a mixture of an organic tellurium compound represented by the general formula (1) and an azo polymerization initiator, (c) a mixture of an organic tellurium compound represented by the general formula (1) and an organic ditellurium compound represented by the general formula (7), and (d) a mixture of an organic tellurium compound represented by the general formula (1), an azo polymerization initiator, and an organic ditellurium compound represented by the general formula (7).

The organic tellurium compound represented by the general formula (1) and for use in the step (I) is as described previously.

The organic ditellurium compound represented by the general formula (7) and for use in the step (I) is as described previously.

Any azo polymerization initiator can be used in the step (I) without particular limitation insofar as it is usable in usual radical polymerization. Examples thereof include 2,2'-azobis-isobutyronitrile (AIBN),
2,2'-azobis(2-methylbutyronitrile) (AMBN),
2,2'-azobis(2,4-dimethylvaleronitrile) (ADVN),
1,1'-azobis(1-cyclohexanecarbonitrile) (ACHN),
dimethyl-2,2'-azobisisobutyrate (MAIB),
4,4'-azobis(4-cyanovaleric acid) (ACVA),
1,1'-azobis(1-acetoxy-1-phenylethane),
2,2'-azobis(2-methylbutylamide), 2,2'-azobis(4-methoxy-2,4-dimethylvaleronitrile) (V-70),
2,2'-azobis(2-methylamidinopropane) dihydrochloride,
2,2'-azobis[2-(2-imidazoline-2-yl)propane],
2,2'-azobis[2-methyl-N-(2-hydroxyethyl)propionamide],
2,2'-azobis(2,4,4-trimethylpentane),
2-cyano-2-propylazoformamide,
2,2'-azobis(N-butyl-2-methylpropionamide), and
2,2'-azobis(N-cyclohexyl-2-methylpropionamide).

There is no particular limitation as to the type of vinyl monomer for use in the step (I) insofar as it is radically polymerizable, but a water-soluble vinyl monomer is preferably used.

In the present invention, the term "vinyl monomer" refers to a monomer whose molecule has a radically polymerizable carbon-carbon double bond. The term "(meth)acrylic" refers to "at least one of acrylic and methacrylic" and the term "(meth)acrylic acid" refers to "at least one of acrylic acid and methacrylic acid". The term "(meth)acrylamide" refers to "at least one of acrylamide and methacrylamide".

Specifically, the water-soluble vinyl monomer is at least one selected from (meth)acrylic acid; hydroxyl group-containing water-soluble (meth)acrylic acid esters, such as hydroxyethyl (meth)acrylate and hydroxypropyl (meth)acrylate; polyethylene glycol methyl ether (meth)acrylate; (meth)acrylamide; N-alkyl (meth)alkylamide; N,N-dialkyl (meth)acrylamide; non-(meth)acrylic nitrogen-containing water-soluble monomers, such as 1-vinyl-2-pyrrolidone, vinylpyridine, vinylpiperidine, vinylimidazole, N-vinyl-ε-caprolactam, and N-vinylformamide; non-(meth)acrylic sulfur-containing water-soluble monomers, such as vinyl sulfonic acid and styrene sulfonic acid; acryloylmorpholine; 2-methacryloyloxyethyl phosphorylcholine; and so on.

In the step (I), a vinyl monomer and an organic tellurium compound represented by the general formula (1) are mixed in a vessel inside of which the atmosphere is replaced with an inert gas, and an azo polymerization initiator and/or an organic ditellurium compound represented by the general formula (7) is further mixed depending on the type of the vinyl monomer and for the purpose of promoting the reaction, controlling the molecular weight or other purposes. In this case, examples of the inert gas include nitrogen, argon, and helium. The preferred inert gases are argon and nitrogen. The more preferred inert gas is nitrogen.

The amount of vinyl monomer used in the above cases (a), (b), (c), and (d) can be appropriately adjusted according to the physical properties of a desired vinyl polymer. Generally, the amount of vinyl monomer used may be, for example, 5 mol to 30,000 mol relative to 1 mol of organic tellurium compound represented by the general formula (1). The amount of vinyl monomer used is preferably 20 mol to 10,000 mol and more preferably 50 mol to 5,000 mol.

In the case of using an organic tellurium compound represented by the general formula (1) and an azo polymerization initiator in combination, the amount of azo polymerization initiator used may be generally, for example, 0.01 mol to 10 mol relative to 1 mol of organic tellurium compound represented by the general formula (1). Preferably, the amount of azo polymerization initiator is 0.05 mol to 2 mol.

In the case of using an organic tellurium compound represented by the general formula (1) and an organic ditellurium compound represented by the general formula (7) in combination, the amount used of organic ditellurium compound represented by the general formula (7) may be generally, for example, 0.01 mol to 100 mol relative to 1 mol of organic tellurium compound represented by the general formula (1). The amount used is preferably 0.1 mol to 10 mol.

In the case of using an organic tellurium compound represented by the general formula (1), an organic ditellurium compound represented by the general formula (7), and an azo polymerization initiator in combination, the amount of azo polymerization initiator used may be generally 0.01 mol to 100 mol relative to 1 mol in total of the organic tellurium compound represented by the general formula (1) and the organic ditellurium compound represented by the general formula (7). The amount used is preferably 0.05 mol to 2 mol.

The step (I) can be performed even in the absence of solvent or using a solvent commonly used for radical polymerization, but may be performed by stirring the above mixture or the like using an aqueous vehicle. Examples of the aqueous vehicle include water and a mixed vehicle of water and a water-soluble solvent. Preferred among them is water.

Examples of the water-soluble solvent include: alcohols, such as methanol, ethanol, 1-propanol, 2-propanol (isopropyl alcohol), 1-butanol, 2-butanol (sec-butyl alcohol), 2-methyl-1-propanol (isobutyl alcohol), and 2-methyl-2-propanol (tert-butyl alcohol); alkoxy alcohols, such as 2-ethoxyethanol, 2-butoxyethanol, 3-methoxy-1-propanol, 1-methoxy-2-propanol, and 1-ethoxy-2-propanol; ketols, such as diacetone alcohol; and ketones, such as acetone, methyl ethyl ketone, and methyl isobutyl ketone. These water-soluble solvents may be used singly or in a mixture of two or more of them.

The amount of solvent used is appropriately adjusted and is generally in a range of 0.01 mL to 50 mL relative to 1 g of vinyl monomer.

The amount of aqueous vehicle used is also not particularly limited, but is preferably in a range of 0.01 mL to 50 mL, more preferably 1 mL to 50 mL, and still more preferably 3 mL to 50 mL relative to 1 g of vinyl monomer. Also when the amount of aqueous vehicle used is the above lower limit or more as just described, the organic tellurium compound according to the present invention used as a living radical polymerization initiator can more stably promote the polymerization of a vinyl monomer in the aqueous vehicle.

An organic tellurium compound represented by the general formula (1) and for use in the step (I) can be generated also by neutralizing, in the solution in the step (I), a carboxylic acid obtained in the step (C) of the above-described production process of an organic tellurium compound. The amount of base in the solution in the step (I) is sufficient if it is an amount at which the above carboxylic acid can be neutralized.

The reaction temperature and the reaction time are appropriately adjusted depending on the molecular weight or molecular weight distribution of a desired vinyl polymer, but the mixture is generally stirred in a range of 0° C. to 150° C. for 1 minute to 100 hours.

Because the growing ends of the vinyl polymer to be obtained by the step (I) have the form of —TeR$^3$ (where the group represented by R$^3$ is the same group as R$^3$ in the general formula (1) and is hereinafter referred to as a tellurium group) derived from an organic tellurium compound represented by the general formula (1), the tellurium groups can be used as a macro living radical polymerization initiator. In other words, an A-B block copolymer, an A-B-A triblock copolymer, an A-B-C triblock copolymer, and the like can be produced using a macro living radical polymerization initiator.

After the end of the step (I), the desired vinyl polymer can be extracted by removing the solvent used and the remaining monomer from the polymerization solution under reduced pressure or can be isolated by a reprecipitation treatment using a solvent in which the desired vinyl polymer is insoluble.

The method for producing a vinyl polymer according to the present invention preferably further includes the step (II) of allowing a reductant to act on the vinyl polymer obtained in the step (I). The reason for this is that operations in the air after the end of the step (I) gradually deactivate the growing ends of the obtained vinyl polymer, but the reductant acts on the tellurium groups at the growing ends of the vinyl polymer to convert the tellurium groups to an organic ditellurium compound and thus enable the removal of the tellurium groups in the form of an organic ditellurium compound from the growing ends of the vinyl polymer and the organic ditellurium compound can be recovered at a high efficiency by washing in the later step.

The step (II) may be performed by isolating the vinyl polymer from the polymerization solution after the end of the step (I) and dissolving it in a solvent or may be performed using the solution after the living radical polymerization, but is, from the viewpoint of reducing the number of process steps, preferably performed by adding a reductant to the polymerization solution after the end of the step (I) to cause a reaction.

Reductants that can be used in the step (II) are compounds capable of reducing the tellurium groups at the growing ends of the vinyl polymer and are those commonly known as reductants. For example, at least one selected from borohydride compounds and organic tellurol compounds can be used as a reductant.

Examples of borohydride compounds include borane complexes (such as borane-dimethyl sulfide complex and borane-tetrahydrofuran complex), diborane, lithium borohydride, sodium borohydride, potassium borohydride, calcium borohydride, sodium triacetoxyborohydride, sodium cyanoborohydride, lithium tri(sec-butyl)borohydride, potassium tri(sec-butyl)borohydride, lithium triethylborohydride, zinc borohydride, tetramethylammonium borohydride, tetraethylammonium borohydride, tetrabutylammonium borohydride, trimethyloctylammonium borohydride, and trimethylbenzylammonium borohydride. Of these, sodium borohydride and lithium triethylborohydride are preferred from the viewpoints of safety, economy, handleability, and so on.

An example of an organic tellurol compound is an organic tellurol compound represented by the general formula (8) below.

[Chem. 14]

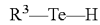
$R^3$—Te—H  Formula (8)

In the general formula (8), the group represented by $R^3$ is the same group as $R^3$ in the general formula (1).

An organic tellurol compound represented by the general formula (8) can be produced by reducing an organic ditellurium compound represented by the general formula (7) with a borohydride compound or the like.

The organic tellurol compound represented by the general formula (8) may be generated in a reaction system. For example, there is a method for generating an organic tellurol compound represented by the general formula (8) in a reaction system using a mixture of a tellurium compound represented by the general formula (9) below and an alcohol or a mixture of an organic ditellurium compound represented by the general formula (7) and a borohydride compound.

[Chem. 15]

$R^3$—Te—$Y^2$  Formula (9)

In the general formula (9), the group represented by $R^3$ is the same group as $R^3$ in the general formula (1).

A leaving group represented by $Y^2$ in the general formula (9) may be any leaving group that can leave in a polymer solution, resulting in generation of an organic tellurol compound represented by the general formula (8), and an example thereof is a trimethylsilyl (TMS) group. The TMS group can leave by reaction with an alcohol, such as methanol, resulting in generation of an organic tellurol compound represented by the general formula (8).

A tellurium compound represented by the general formula (9) can be produced by reacting an organic ditellurium compound represented by the general formula (7) with a reductant and subsequently reacting the obtained product with a silylation agent.

Examples of the reductant for use in producing a tellurium compound represented by the general formula (9) include: lithium metal; sodium metal; potassium metal; naphthalenides of these metals; and metallic hydrides, such as sodium borohydride, lithium borohydride, potassium borohydride, lithium triethylborohydride, and sodium cyanoborohydride. Preferred among them is lithium triethylborohydride.

Examples of the silylation agent include trimethylsilyl chloride, trimethylsilyl bromide, and triethylsilyl bromide. The preferred silylation agent is trimethylsilyl bromide.

A specific example of a method for producing a tellurium compound represented by the general formula (9) is the following method.

First, an organic ditellurium compound represented by the general formula (7) is dissolved in a solvent. Examples of the solvent that can be used include: polar solvents, such as dimethylformamide (DMF); aromatic solvents, such as toluene and xylene; aliphatic hydrocarbons, such as hexane and dimethoxyethane; and ethereal solvents, such as diethyl ether and tetrahydrofuran (THF). The amount of solvent used is appropriately adjusted, but is, generally, preferably 1 ml to 500 ml relative to 1 g of the organic ditellurium compound represented by the general formula (7).

Next, a reductant is slowly added dropwise to the above solution and the mixture is stirred. The reaction time varies according to the reaction temperature, but is, generally, preferably 5 minutes to 24 hours. The reaction temperature is preferably 0° C. to 80° C.

Next, a silylation agent is added to the above reaction liquid and the mixture is stirred. The reaction time varies according to the reaction temperature, but is, generally, preferably 5 minutes to 24 hours. The reaction temperature is preferably 0° C. to 80° C.

After the completion of the reaction, the solvent is concentrated to isolate and purify a desired product. Before the solvent concentration, washing with water, brine or the like may be appropriately performed. The purification method can be appropriately selected depending on the compound, but is generally preferably effected by distillation under reduced pressure, recrystallization or so on.

The amount of solvent used in the step (II) is appropriately adjusted and is, for example, relative to 1 g of vinyl polymer, generally preferably in a range of 0.01 ml to 100 ml.

In the step (II), stirring is preferably performed, generally, at temperature in a range of 0° C. to 100° C. for 5 minute to 24 hours.

The amount of reductant used in the step (II) is preferably 0.5 mol to 10.0 mol relative to 1 mol of organic tellurium compound represented by the general formula (1).

The method for producing a vinyl polymer according to the present invention preferably further includes the step (III) of washing the vinyl polymer obtained in the step (II). The washing method that can be used is any known washing method, but is preferably washing by liquid-liquid extraction. The washing by liquid-liquid extraction is preferably performed using a solution obtained by isolating the vinyl polymer from the solution after the end of the step (II) and dissolving the isolated vinyl polymer in a suitable solvent or using the solution after the end of the step (II).

An example of the above washing by liquid-liquid extraction is the method of mixing a solvent containing a vinyl polymer dissolved therein and a solvent capable of phase separation with the solvent dissolving a vinyl polymer, and then extracting the separated solvents. Through this operation, an organic ditellurium compound can be removed from the vinyl polymer. The removal of the organic ditellurium compound is more effectively achieved by repeating the washing by liquid-liquid extraction. When, after the washing by liquid-liquid extraction, the solvents in different phases are each removed under reduced pressure, the vinyl polymer and the organic ditellurium compound can be separately recovered.

The solvent for the above liquid-liquid extraction may be any aprotic solvent or protic solvent that can dissolve a vinyl polymer.

Examples of the aprotic solvent that can be used include benzene, toluene, N,N-dimethylformamide (DMF), dimethyl sulfoxide (DMSO), acetone, 2-butanone (methyl ethyl ketone), dioxane, chloroform, carbon tetrachloride, tetrahydrofuran (THF), ethyl acetate, and propylene glycol monomethyl ether acetate.

Examples of the protic solvent that can be used include water, methanol, ethanol, isopropanol, n-butanol, ethyl cellosolve, butyl cellosolve, 1-methoxy-2-propanol, diacetone alcohol, and acetonitrile.

Examples of the solvent capable of phase separation with the solvent dissolving a vinyl polymer include: aliphatic hydrocarbons, such as pentane, hexane, heptane, octane, nonane, and decane; aromatic hydrocarbons, such as benzene and toluene; chloroform; and carbon tetrachloride. Preferred among them are hexane, heptane, octane, and toluene. More preferred is heptane.

In the above washing by liquid-liquid extraction, the solvent capable of phase separation is preferably added, generally, 0.1 times to 10 times more than the solvent phase dissolving a vinyl polymer. The washing by liquid-liquid extraction is preferably performed, generally, at 10° C. to 60° C.

Since the recovered tellurium compound is a high-purity organic ditellurium compound, it can be easily regenerated as an organic tellurium compound (living radical polymerization initiator), for example, using the method disclosed in Published Japanese Patent Application No. 2004-323437.

The method for producing a vinyl polymer according to the present invention enables, with the use of an organic tellurium compound represented by the general formula (1), suitable polymerization of, particularly, water-soluble vinyl monomers.

The molecular weight of the vinyl polymer obtained by the production method according to the present invention can be appropriately adjusted by the reaction time and the amount of organic tellurium compound. For example, a vinyl polymer having a number average molecular weight (Mn) of 500 to 1,000,000 can be obtained by the production method according to the present invention. The production method according to the present invention is particularly suitable for obtaining a vinyl polymer having a Mn of 1,000 to 50,000. The value of Mn can be measured by the gel permeation chromatography (hereinafter, referred to as "GPC") method.

As for the vinyl polymer to be obtained by the production method according to the present invention, its molecular weight distribution (PDI) can be controlled to 2.0 or less and is preferably 1.5 or less. The molecular weight distribution (PDI) is obtained by (the weight-average molecular weight (Mw) of the vinyl polymer)/(the number average molecular weight (Mn) of the vinyl polymer). As the PDI is smaller, a vinyl polymer having a narrower molecular weight distribution width and therefore closer molecular weights can be obtained. When the value of PDI is 1.0, the molecular weight distribution width is narrowest. On the contrary, as the PDI is larger, the vinyl polymer includes portions having small molecular weights or large molecular weights as compared to the designed vinyl polymer molecular weight.

Since the method for producing a vinyl polymer according to the present invention includes the step (II) and the step (III), the content of tellurium in the obtained vinyl polymer can be small. Therefore, in this case, the vinyl polymer can be suitably used, for example, for optics, medical treatments, electrics and electronics, and energy materials.

EXAMPLES

The present invention will be described below in further detail with reference to specific examples. The present invention is not at all limited by the following examples and modifications and variations may be appropriately made therein without changing the gist of the invention.

Synthesis of Organic Ditellurium Compound

Synthesis Example 1

A compound represented by the following general formula (10) was synthesized by the procedure below.

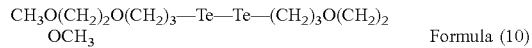

Formula (10)

An amount of 15 g of sodium hydride (60% dispersion in mineral oil, 0.38 mol) and THF (50 mL) were added into a 300-mL three-necked glass flask and this solution was cooled in an ice bath while being stirred. An amount of 26 mL (0.34 mol) of 2-methoxy ethanol was added dropwise over 10 minutes to this solution, aryl bromide (35 mL, 0.41 mmol) was then slowly added dropwise to the solution, and the solution was further stirred at room temperature for three hours. An amount of 50 mL of water was further added to the solution, a product was extracted from the solution with dichloromethane, and the product was dehydrated with magnesium sulfate. Next, the solvent was distilled off and the residue was distilled, thus obtaining 2-methoxyethyl aryl ether (35 g, yield: 88%). $^1$H NMR and $^{13}$C NMR confirmed that the product was a desired product.

Next, 5.3 mL (42 mmol) of the above 2-methoxyethyl aryl ether and THF (50 mL) were added into a 500-mL three-necked glass flask and this solution was cooled in an ice bath while being stirred. A solution of 9-borabicyclo[3.3.1]nonane in THF (100 mL, 50 mmol) was added dropwise over 20 minutes to this solution, and the solution was further stirred at room temperature for three hours. The reaction solution was cooled in an ice bath, 100 mL of 3N sodium hydroxide aqueous solution and 100 mL of hydrogen peroxide water were added to the solution, and the solution was further stirred at room temperature for an hour. A product was extracted from the solution with dichloromethane and the product was dehydrated with magnesium sulfate. Next, the solvent was distilled off and the residue was distilled, thus obtaining 4,7-dioxa-1-octanol (5.1 g, yield: 90%). $^1$H NMR and $^{13}$C NMR confirmed that the product was a desired product.

Next, 8.0 g (60 mmol) of the above 4,7-dioxa-1-octanol and dichloromethane (100 mL) were added into a 300-mL three-necked glass flask and this solution was cooled in an ice bath while being stirred. An amount of 0.35 g (3.0 mmol) of 4-(dimethylamino)pyridine, 0.55 g (6.0 mmol) of trimethylamine hydrochloride, and 17 g (90 mmol) of p-toluenesulfonyl chloride were added to this solution and 13 g (90 mmol) of triethylamine and 20 mL of dichloromethane were then added dropwise over 20 minutes to the solution. The solution was further stirred for two hours in an ice bath. A product was extracted from the solution with dichloromethane and the product was dehydrated with magnesium sulfate. The solvent was distilled off and the residue was purified by column chromatography, thus obtaining 3-(2-methoxyethoxy)propyl 4-methylbenzenesulfonate (15 g, yield: 85%). $^1$H NMR and $^{13}$C NMR confirmed that the product was a desired product.

Next, 2.6 g (20 mmol) of metallic tellurium (trade name: Tellurium (−40 mesh) manufactured by Aldrich), sodium (0.51 g, 22 mmol), and ethylenediamine (75 mL) were added into a 200-mL three-necked glass flask and the mixture was refluxed for three hours while being stirred. The reaction solution was cooled to room temperature, a mixed solution of 3-(2-methoxyethoxy)propyl 4-methylbenzenesulfonate (5.8 g, 20 mmol) obtained in the above manner and THF (25 mL) was added dropwise over 30 minutes, and the resultant reaction solution was stirred at room temperature for an hour. The reaction solution was cooled in an ice bath, 30 mL of water was slowly added to the solution, and the solution was filtered through a short cerite column. A crude product obtained by distilling off the solvent was purified by column chromatography with ethyl acetate, thus obtaining a compound (2,5,14,17-tetraoxa-9,10-ditelluraoctadecane) represented by the general formula (10) (7.0 g, yield: 71%). $^1$H NMR and $^{13}$C NMR confirmed that the product was a desired product.

Synthesis of Organic Tellurium Compound

Synthesis Example 2

A compound (hereinafter, referred to as Int1) represented by the following formula was synthesized by the procedure below. Me in the following formula refers to a methyl group.

[Chem. 16]

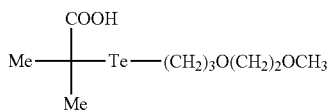

Int 1

Diisopropylamine (2.5 mL, 18 mmol) and THF (50 mL) were added into a 500-mL three-necked glass flask and this solution was cooled in an ice bath while being stirred. A solution of butyllithium in hexane (10.5 mL, 16.5 mmol) was added dropwise over 10 minutes into this flask, triethylsilyl isobutyrate (3.6 mL, 16.5 mmol) was then slowly added dropwise into this flask, and the solution was further stirred for an hour.

The above 2,5,14,17-tetraoxa-9,10-ditelluraoctadacane (1.5 mL, 7.5 mmol) and THF (150 mL) were added into a 200-mL three-necked glass flask and this solution was cooled in an ice bath while being stirred. Bromine (0.40 mL, 7.9 mmol) was added dropwise to this solution and the solution was further stirred for an hour. This reaction solution was added dropwise to the above-described solution prepared in the 500-mL three-necked glass flask being cooled in a dry ice/acetone bath. The reaction solution was increased in temperature by changing the bath for cooling to an ice bath and further stirred for 30 minutes.

A 1M hydrochloric acid aqueous solution (0.5 mL) was added to the reaction solution, the mixture was stirred for 30 minutes, and a saturated sodium hydrogen carbonate aqueous solution and dichloromethane were added in this order to the mixture to eliminate an organic phase. A hydrochloric acid aqueous solution and dichloromethane were further added to an aqueous phase and an organic phase was dehydrated with magnesium sulfate. The solvent was distilled off to obtain Int1 (4.4 g, yield: 80%). $^1$H NMR and $^{13}$C NMR confirmed that the product was a desired product.

Synthesis Example 3

A compound (hereinafter, referred to as Int2) represented by the following formula was synthesized by the procedure below. In the following formula, M represents a methyl group and Ph represents a phenyl group.

[Chem. 17]

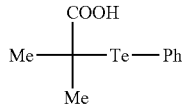

Int2

Diisopropylamine (2.5 mL, 18 mmol) and THF (50 mL) were added into a 500-mL three-necked glass flask and this solution was cooled in an ice bath while being stirred. A solution of butyllithium in hexane (10.5 mL, 16.5 mmol) was added dropwise over 10 minutes into this flask, triethylsilyl isobutyrate (3.6 mL, 16.5 mmol) was then slowly added dropwise into this flask, and the solution was further stirred for an hour.

Diphenyl ditelluride (3.1 g, 7.5 mmol) and THF (150 mL) were added into a 200-mL three-necked glass flask and this solution was cooled in an ice bath while being stirred. Bromine (0.40 mL, 7.9 mmol) was added dropwise to this solution and the solution was further stirred for an hour. This reaction solution was added dropwise to the above-described solution prepared in the 500-mL three-necked glass flask being cooled in a dry ice/acetone bath. The reaction solution was increased in temperature by changing the bath for cooling to an ice bath and further stirred for 30 minutes.

A 1M hydrochloric acid aqueous solution (0.5 mL) was added to the reaction solution, the mixture was stirred for 30 minutes, and a saturated sodium hydrogen carbonate aqueous solution and dichloromethane were added in this order to the mixture to eliminate an organic phase. A hydrochloric acid aqueous solution and dichloromethane were further added to an aqueous phase and an organic phase was dehydrated with magnesium sulfate. The solvent was distilled off to obtain Int2 (3.6 g, yield: 82%). $^1$H NMR and $^{13}$C NMR confirmed that the product was a desired product.

Synthesis of Vinyl Polymer

Example 1

N-vinyl-2-pyrrolidone (0.43 mL, 4 mmol), 4,4'-azobis(4-cyanovaleric acid) (1.1 mg, 4 μmol), 1.5 mL of sodium carbonate/sodium hydrogen carbonate buffer solution (aqueous solution), and Int1 (6.6 mg, 20 μmop were introduced into a Pyrex (registered trademark) glass tube inside which the atmosphere was replaced with nitrogen. This solution was stirred at 65° C. for 16 hours. GPC analysis confirmed that Mn=18500 and PDI=1.10. The amount of aqueous vehicle used in Example 1 was 3.37 mL in terms of per gram of monomer.

Example 2

An amount of 284 mg (4 mmol) of acrylamide, 1.1 mg (4 μmol) of 4,4'-azobis(4-cyanovaleric acid), 1.5 mL of deionized water, and 6.6 mg (20 μmop of sodium salt of Int1 were introduced into a Pyrex (registered trademark) glass tube inside which the atmosphere was replaced with nitrogen. This solution was stirred at 65° C. for five hours. GPC analysis confirmed that Mn=12700 and PDI=1.19. The amount of aqueous vehicle used in Example 2 was 5.28 mL in terms of per gram of monomer.

Example 3

An amount of 0.41 mL (4 mmol) of dimethylacrylamide, 1.1 mg (4 μmop of 4,4'-azobis(4-cyanovaleric acid), 2.4 mg (28 μmol) of sodium hydrogen carbonate, 1.0 mL of deionized water, and 6.6 mg (20 μmol) of Int1 were introduced into a Pyrex (registered trademark) glass tube inside which the atmosphere was replaced with nitrogen. This solution was stirred at 65° C. for 1.5 hours. GPC analysis confirmed that Mn=17200 and PDI=1.20. The amount of aqueous vehicle used in Example 3 was 2.52 mL in terms of per gram of monomer.

Example 4

An amount of 0.41 mL (4 mmol) of dimethylacrylamide, 1.1 mg (4 μmol) of 4,4'-azobis(4-cyanovaleric acid), 1.5 mL of deionized water, and 6.6 mg (20 μmol) of sodium salt of Int1 were introduced into a Pyrex (registered trademark) glass tube inside which the atmosphere was replaced with nitrogen. This solution was stirred at 65° C. for 1.5 hours. GPC analysis confirmed that Mn=13200 and PDI=1.21. The amount of aqueous vehicle used in Example 4 was 3.78 mL in terms of per gram of monomer.

Example 5

An amount of 0.41 mL (4 mmol) of methacrylamide, 1.1 mg (4 μmol) of 4,4'-azobis(4-cyanovaleric acid), 2.4 mg (28 μmol) of sodium hydrogen carbonate, 1.0 mL of deionized water, and Int1 (6.6 mg, 20 μmol) were introduced into a Pyrex (registered trademark) glass tube inside which the atmosphere was replaced with nitrogen. This reaction solution was stirred at 65° C. for two hours. GPC analysis confirmed that Mn=18100 and PDI=1.46. The amount of aqueous vehicle used in Example 5 was 2.94 mL in terms of per gram of monomer.

Example 6

An amount of 0.43 mL (4 mmol) of 2-hydroxyethyl acrylate, 1.1 mg (4 μmol) of 4,4'-azobis(4-cyanovaleric acid), 1.5 mL of deionized water, and 6.6 mg (20 μmol) of sodium salt of Int1 were introduced into a Pyrex (registered trademark) glass tube inside which the atmosphere was replaced with nitrogen. This solution was stirred at 65° C. for eight hours. GPC analysis confirmed that Mn=17200 and PDI=1.27. The amount of aqueous vehicle used in Example 6 was 3.23 mL in terms of per gram of monomer.

Comparative Example 1

An amount of 0.43 mL (4 mmol) of N-vinyl-2-pyrrolidone, 1. 1 mg (4 μmol) of 4,4'-azobis(4-cyanovaleric acid), 1.5 mL of sodium carbonate/sodium hydrogen carbonate buffer solution (aqueous solution), and Int2 (5.8 mg, 20 μmol) were introduced into a Pyrex (registered trademark) glass tube inside which the atmosphere was replaced with nitrogen. This solution was stirred at 65° C. for 16 hours, but the reaction did not proceed. The amount of aqueous vehicle used in Comparative Example 1 was 3.37 mL in terms of per gram of monomer.

Comparative Example 2

An amount of 0.41 mL (4 mmol) of methacrylamide, 1.1 mg (4 μmol) of 4,4'-azobis(4-cyanovaleric acid), 2.4 mg (28 μmol) of sodium hydrogen carbonate, 1.0 mL of deionized water, and Int2 (5.8 mg, 20 μmol) were introduced into a Pyrex (registered trademark) glass tube inside which the atmosphere was replaced with nitrogen. This reaction solution was stirred at 65° C. for two hours. During polymerization reaction, gelation was observed. GPC analysis confirmed that Mn=8700 and PDI=1.50. As just described, in Comparative Example 2, gelation was observed during polymerization reaction, so that the polymerization reaction did not sufficiently proceed. The amount of aqueous vehicle used in Comparative Example 2 was 2.94 mL in terms of per gram of monomer.

As is obvious from Examples 1 to 6, it was confirmed that when an organic tellurium compound (Int1) according to the present invention was used as a living radical polymerization initiator, the polymerization of a vinyl monomer stably proceeded even at a large amount of aqueous vehicle used.

On the contrary, in Comparative Examples 1 and 2 in which Int2 was used as a living radical polymerization initiator, the polymerization of a vinyl monomer did not stably proceed.

The number average molecular weight (Mn) and molecular weight distribution (PDI) in each of Examples 1 and 6 and Comparative Example 1 were determined based on the molecular weight of a poly(methyl methacrylate) standard sample (Shodex PMMS Standard) using GPC [Shodex GPC-104 (columns: Shodex LF-604×2) and Shodex GPC-101 (columns: Shodex LF-804, K-805F, and K-800RL)].

The number average molecular weight (Mn) and molecular weight distribution (PDI) in each of Examples 2 to 5 and Comparative Example 2 were determined based on the molecular weight of a polyethylene glycol standard sample (TOSOH Tskgel, Scientific Polymer Products, WAKO NIMI J CRM) using GPC [Shodex GPC-101 (columns: Shodex OHpak SB-806M HQ x 2 and Shodex OHpak SB-804M HQ)].

The invention claimed is:
1. An organic tellurium compound represented by the following general formula (1):

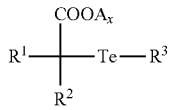

Formula (1)

where in the general formula (1) $R^1$ and $R^2$ each independently represent a hydrogen atom or an alkyl group having 1 to 8 carbon atoms, A represents an alkali metal atom or an alkaline earth metal atom, x=1 when A is monovalent, x=½ when A is divalent, and $R^3$ is represented by the following general formula (2), general formula (3) or general formula (4):

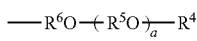

Formula (2)

where in the general formula (2) $R^4$ represents a hydrogen atom or an alkyl group having 1 to 8 carbon atoms, $R^5$ and $R^6$ each independently represent an alkylene group having 2 to 8 carbon atoms, and a represents an integer from 0 to 10,

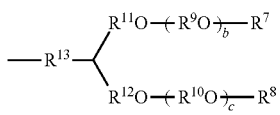

Formula (3)

where in the general formula (3) $R^7$ and $R^8$ each independently represent a hydrogen atom or an alkyl group having 1 to 8 carbon atoms, $R^9$, $R^{10}$, $R^{11}$, $R^{12}$ each independently represent an alkylene group having 2 to 8 carbon atoms, $R^{13}$ represents an alkylene group having 1 to 8 carbon atoms, and b and c each independently represent an integer from 0 to 10,

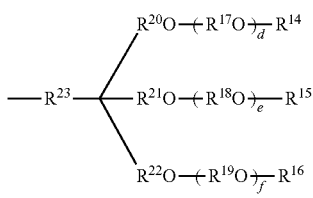

Formula (4)

where in the general formula (4) $R^{14}$, $R^{15}$, and $R^{16}$ each independently represent a hydrogen atom or an alkyl group having 1 to 8 carbon atoms, $R^{17}$, $R^{18}$, $R^{19}$, $R^{20}$, $R^{21}$, and $R^{22}$ each independently represent an alkylene group having 2 to 8 carbon atoms, $R^{23}$ represents an alkylene group having 1 to 8 carbon atoms, and d, e, and f each independently represent an integer from 0 to 10.

2. A method for producing the organic tellurium compound according to claim 1, the method including the steps of: (A) reacting a compound represented by a general formula (5) below with a base; (B) reacting a compound obtained by the step (A) with a compound represented by a general formula (6) below; (C) removing a protective group on a carboxyl group in a compound obtained by the step (B), thus deprotecting the carboxyl group; and (D) neutralizing a carboxylic acid obtained by the step (C):

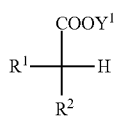

Formula (5)

where in the general formula (5) $R^1$ is the same as $R^1$ in the general formula (1), $R^2$ is the same as $R^2$ in the general formula (1), and $Y^1$ represents a protecting group,

Formula (6)

where in the general formula (6) $R^3$ is the same as $R^3$ in the general formula (1), and X represents a halogen atom.

3. A living radical polymerization initiator made of the organic tellurium compound according to claim 1.

4. A method for producing a vinyl polymer, the method including the step of polymerizing a vinyl monomer by a living radical polymerization using the organic tellurium compound according to claim 1 to synthesize a vinyl polymer.

5. The method for producing a vinyl polymer according to claim 4, wherein the vinyl monomer is a water-soluble vinyl monomer.

6. The method for producing a vinyl polymer according to claim 4, wherein the living radical polymerization is performed in an aqueous vehicle.

7. A vinyl polymer obtained by the method for producing a vinyl polymer according to claim 4.

* * * * *